(12) United States Patent
Grazioso et al.

(10) Patent No.: US 7,759,647 B2
(45) Date of Patent: Jul. 20, 2010

(54) PET IMAGING SYSTEM WITH APD-BASED PET DETECTORS AND THREE-DIMENSIONAL POSITRON-CONFINING MAGNETIC FIELD

(75) Inventors: Ron Grazioso, Knoxville, TN (US); Mehmet Aykac, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/657,155

(22) Filed: Jan. 24, 2007

(65) Prior Publication Data

US 2008/0173819 A1    Jul. 24, 2008

(51) Int. Cl.
*G01T 1/164*    (2006.01)
(52) U.S. Cl. .................................. 250/363.05
(58) Field of Classification Search ............. 250/363.05
See application file for complete search history.

(56) References Cited

U.S. PATENT DOCUMENTS 4,743,851 A * 5/1988 Lim et al. ................... 324/309
5,055,789 A * 10/1991 Kondo et al. ................ 324/309
5,530,355 A * 6/1996 Doty .......................... 324/318

OTHER PUBLICATIONS

Pratte et al. Front-end electronics for the RatCAP mobile animal PET scanner, IEEE Transactions on Nuclear Science vol. 51, No. 4 (Oct. 2004), pp. 1318-1323.*
Schlyer et al. Development of a simultaneous PET/MRI scanner, 2004 IEEE Nuclear Science Symposium Conference Record, vol. 6 (2004), pp. 3419-3421.*
Hamamatsu Si APD Array S8550 data sheet (Jun. 2006).*

* cited by examiner

*Primary Examiner*—David P Porta
*Assistant Examiner*—Shun Lee

(57) ABSTRACT

PET detector modules are provided within a multi-dimensional magnetic field, to confine the range of emitted positrons from an object being imaged to improve spatial resolution of reconstructed PET images. Each module includes a number of independent, optically isolated detectors. Each detector includes an array of scintillator crystals read out by an array of APDs (avalanche photodiodes).

13 Claims, 3 Drawing Sheets

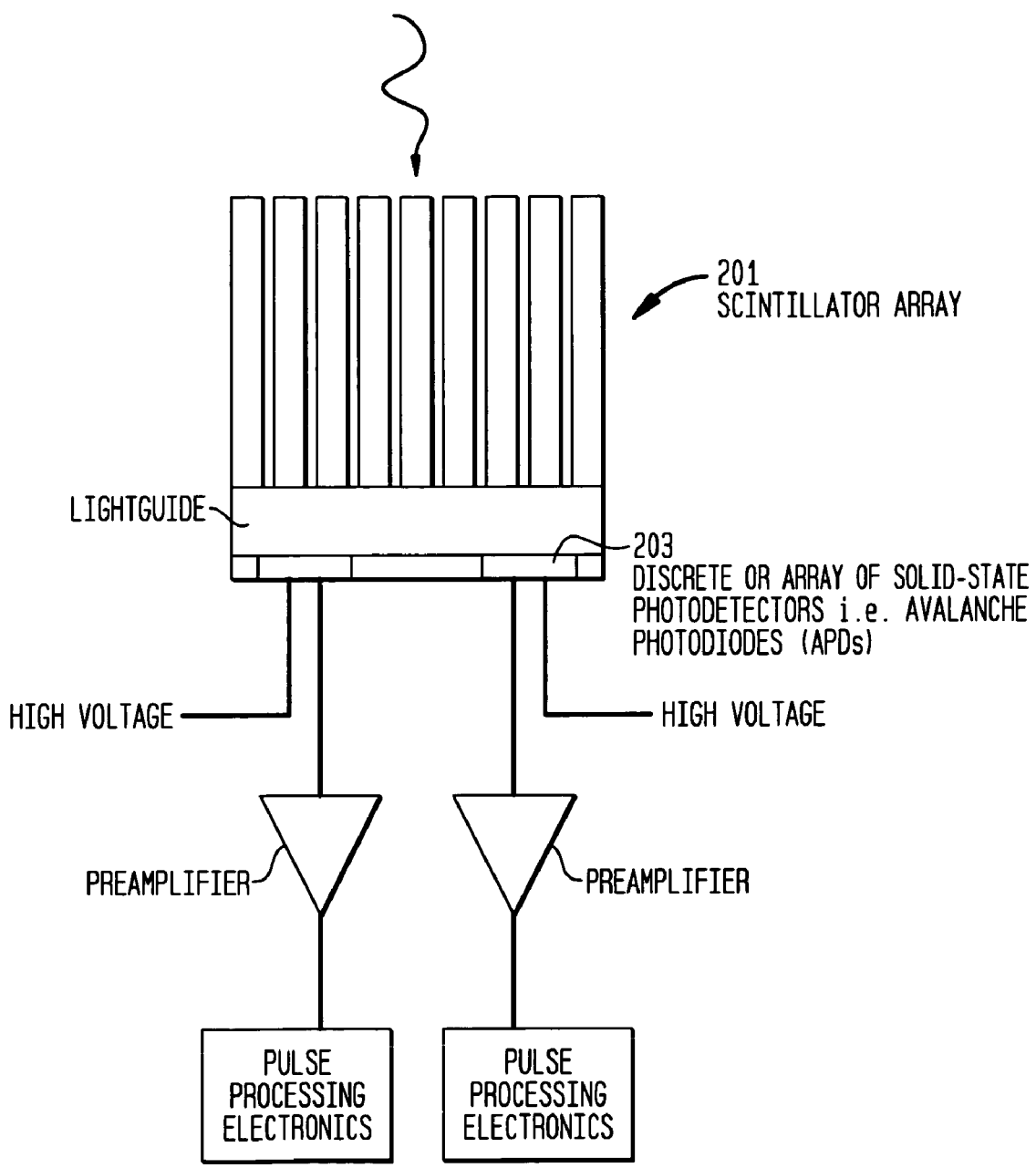

PET IMAGING SYSTEM WITH APD-BASED PET DETECTORS AND THREE-DIMENSIONAL POSITRON-CONFINING MAGNETIC FIELD

FIELD OF THE INVENTION

The present invention generally relates to the field of medical imaging, and systems for obtaining diagnostic images such as nuclear medicine images. In particular, the present invention relates to imaging systems and methods for obtaining diagnostic images such as nuclear medicine images from positron emission tomography (PET) data, with improved spatial resolution.

BACKGROUND OF THE INVENTION

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

One particular nuclear medicine imaging technique is known as Positron Emission Tomography, or PET. PET is used to produce images for diagnosing the biochemistry or physiology of a specific organ, tumor or other metabolically active site. Measurement of the tissue concentration of a positron emitting radionuclide is based on coincidence detection of the two gamma photons arising from positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence event, they also identify a line of response, or LOR, along which the annihilation event has occurred.

An example of a PET method and apparatus is described in U.S. Pat. No. 6,858,847, which patent is incorporated herein by reference in its entirety. After being sorted into parallel projections, the LORs defined by the coincidence events are used to reconstruct a three-dimensional distribution of the positron-emitting radionuclide within the patient. PET is particularly useful in obtaining images that reveal bioprocesses, e.g. the functioning of bodily organs such as the heart, brain, lungs, etc. and bodily tissues and structures such as the circulatory system.

Depending upon the isotope used, the spatial resolution obtainable with PET imaging is currently limited to 1-8 mm. For example, positrons emitted from $^{18}F$ used in FDG (a common radiopharmaceutical used in PET imaging) obtain a resolution of approximately 1 mm FWTM (Full Width at Tenth Maximum) in water, and positrons emitted from $^{15}O$ obtain a resolution of approximately 4 mm FWTM (Full Width at Tenth Maximum) in water. Current commercially available small animal PET systems are able to image close to 1 mm spatial resolution FWHM (Full Width Half Maximum). Some academic proof-of-principle PET detectors are known which can image close to 600 μm; however in real world applications the detectors would not be able to achieve such resolution without limiting positron range.

PET technology advances have included finer detector elements designed to improve spatial resolution. However, there is a limit to what extent reducing detector element size will improve spatial resolution in PET. The spatial resolution of PET imaging is limited by several other factors, such as annihilation photon non-colinearity, positron range, off-axis detector penetration, detector Compton scatter, undersampling of the signal in the linear or angular directions for the image reconstruction process, and patient motion. The overall spatial resolution of the systems is a convolution of these components. Of these other factors that contribute to resolution broadening, perhaps the most uncertain and, for certain isotopes, the most dominant effect is from positron range. Positron range refers to the distance that a positron travels after emission and prior to annihilation by an electron.

In the paper entitled "Combined MRI-PET Scanner: A Monte Carlo Evaluation of the Improvements in PET Resolution Due to the Effects of a Static Homogeneous Magnetic Field," IEEE Transactions on Nuclear Science, Vol. 43, No. 4, August 1996, Raylman et al. simulated the potential improvement to spatial resolution of a PET detector operating inside a static homogeneous magnetic field associated with a magnetic resonance scanner.

Further, U.S. Pat. No. 4,939,464 to Hammer, incorporated herein by reference in its entirety, discloses a combination NMR-PET apparatus wherein a PET detector is located inside a cylindrical magnet of a nuclear magnetic resonance scanner. The '464 patent discloses that in the presence of a magnetic field a positron will not maintain a circular orbit but will spiral towards the center of the orbit, with the result that in the presence of a magnetic field positrons emitted transverse or perpendicular to the magnetic field will be confined to a range defined by the mass, velocity and charge of the positron and the magnetic field.

There remains a need in the art for improvement in spatial resolution of a PET imaging system without combination with a MRI scanner, and beyond the improved resolution observed when a PET system is embedded within the one-dimensional magnetic field of a MRI scanner.

SUMMARY OF THE INVENTION

The present invention provides an APD-based (Avalanche PhotoDiode) PET detector operating within a static, multi-dimensional magnetic field. The multi-dimensional magnetic field confines emitted positrons in multiple directions, thereby improving the spatial resolution of PET images reconstructed from PET data acquired with the PET detector. Because APDs are quite small, a detector could be designed that could fit into the bore of a multi-dimensional magnet. APDs are also magnetically insensitive.

BRIEF DESCRIPTION OF THE DRAWINGS

The invention will now be more fully described by way of example with reference to the accompanying drawings in which:

FIG. 3 is a circuit block diagram of the components of a PET detector module as incorporated in FIG. 2.

DETAILED DESCRIPTION OF THE INVENTION

The present invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention.

The present invention proposes to provide a PET detector apparatus operating within a multi-dimensional magnetic field, such as a three-dimensional magnetic field, so as to confine the range of emitted positrons in more than one direction, thereby further improving the spatial resolution of PET images reconstructed from data acquired with the PET detector apparatus.

Figure 1:
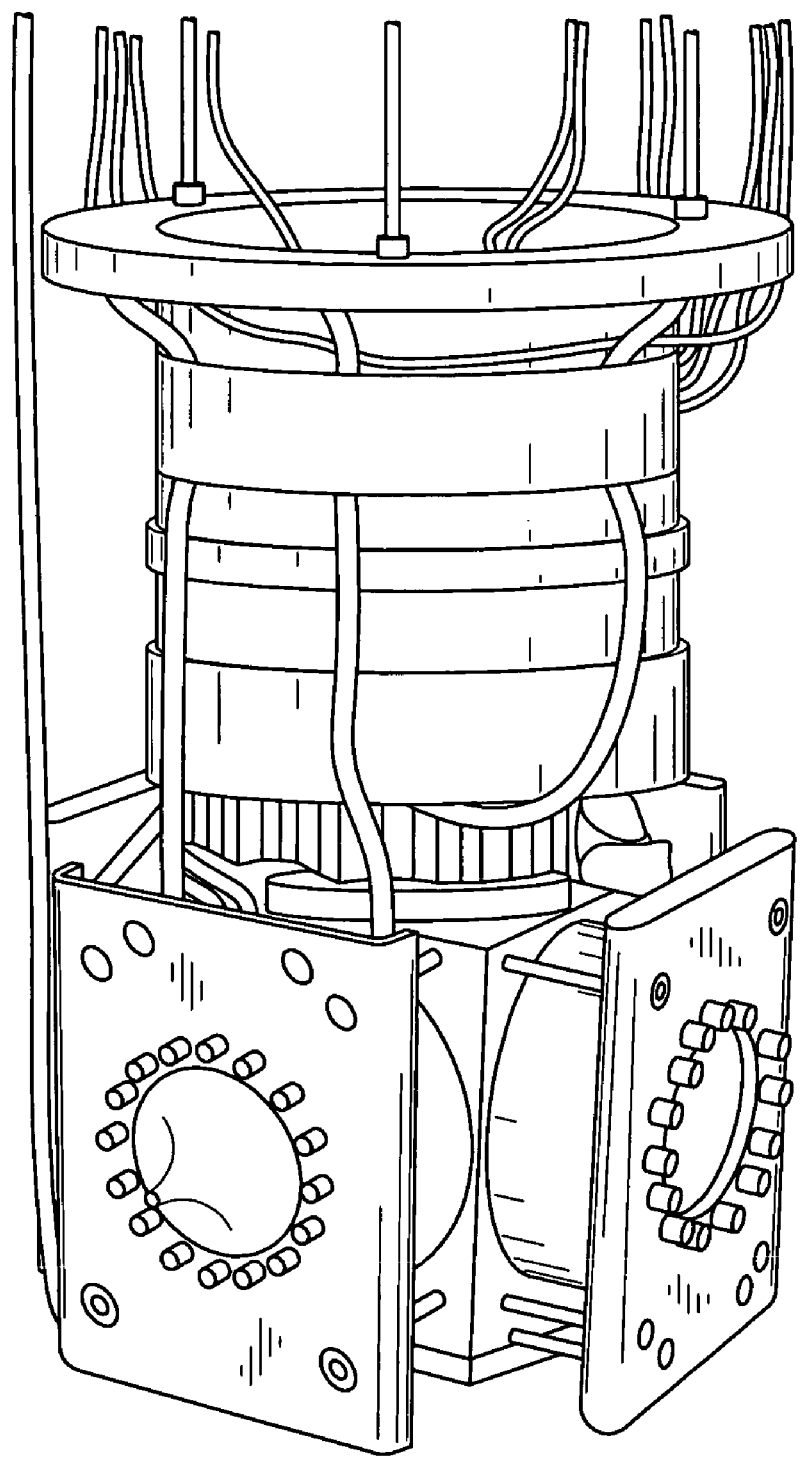
FIG. 1 is a diagram of a three-axis superconducting magnet that can be used in accordance with an embodiment of the invention.

Three-dimensional or 3-axis magnets with bore sizes sufficient to accommodate certain PET imaging applications are generally known in the art. FIG. 1 illustrates an example of a 3-axis superconducting magnet distributed by American Magnetics of Oak Ridge, Tenn. The magnet includes a customizable support structure having 3 sets of helium efficient vapor cooled current leads, magnet dewar and other associated electronics. Typical specifications include high field up to 9 T for the principal axis, 2.0/3.0 inch (~75 mm) vertical clear bore and 1 T rotating vector using any combination of x, y and z-axis magnets. In accordance with the present invention, the magnetic fields along each axis would be static. Larger bore sizes are available with smaller permanent magnets, but which generally have lower magnetic field strengths (e.g., 1-2 Tesla).

Figure 2:
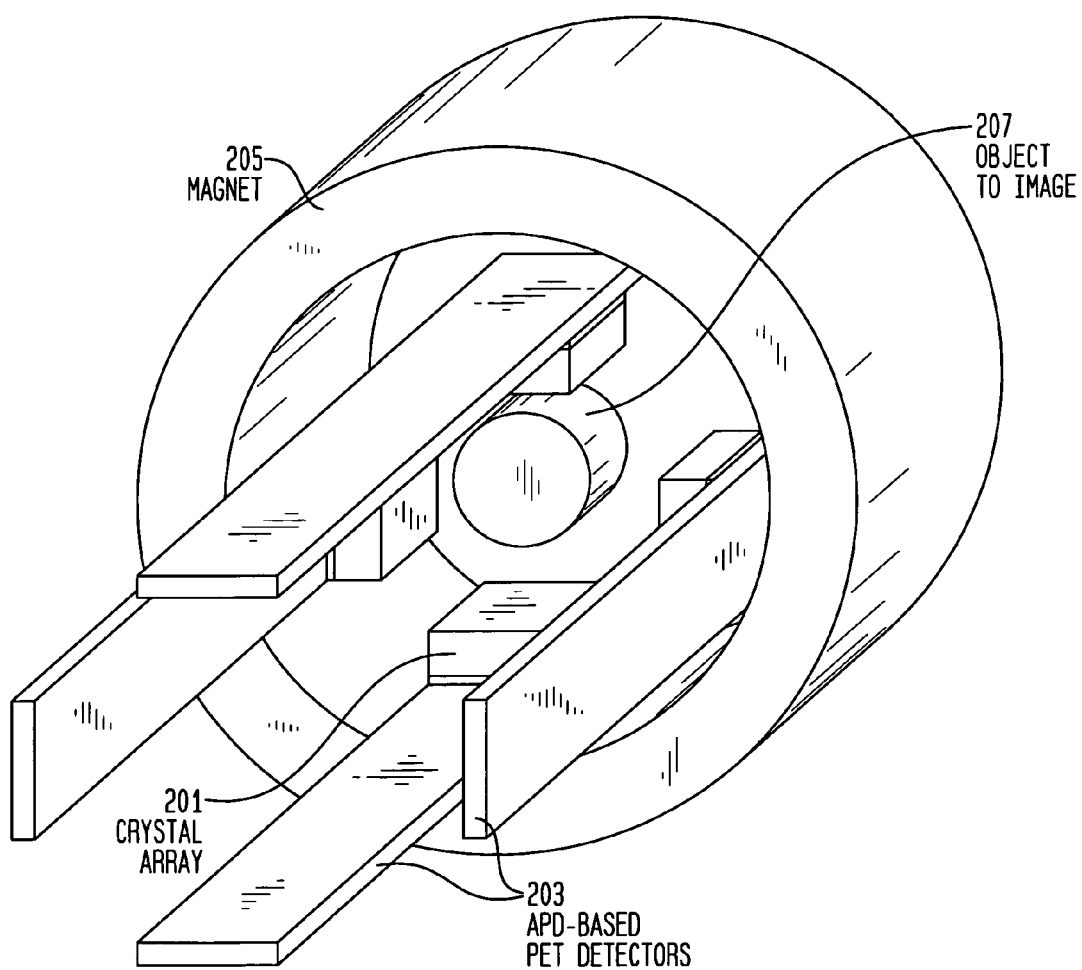
FIG. 2 is a diagram of a positron-confined PET imaging system in accordance with an embodiment of the invention.

FIG. 2 illustrates an example embodiment in accordance with the invention. A PET detector ring including a number of PET detector modules in the form of scintillation crystal arrays 201 and scintillation detectors 203 such as APD-based PET detectors is placed inside the bore of a multi-dimensional permanent magnet 205. Positrons emitted from object 207 being imaged are confined in multiple dimensions by the multi-dimensional magnetic fields produced by the magnet 205. For example, the magnet 205 may be a three-axis permanent magnet as shown in FIG. 1. The improvement in spatial resolution would increase as the magnetic field strength increases. Therefore, a cooled electromagnet could achieve a relatively high magnetic field with a large bore size.

As shown in FIG. 3, each detector module may include a scintillator block 201 that is optically coupled through a light guide to a solid state photodetector or array of photodetectors, such as avalanche photodiodes (APDs) 203 or other semiconductor-based type of photodetector. For purposes of explanation, the example of using APDs will be discussed hereinafter.

Each individual solid-state photodetector may be optically coupled to more than one scintillator, or may be coupled in a one-to-one scintillator to photodetector arrangement. Each APD is electrically connected to a high voltage source. Multiple APDs may share a single voltage source. The charge created in the APDs is collected in a preamplifier, such as a charge-sensitive preamplifier, transimpedance preamplifier or voltage-sensitive preamplifier. The pulse signals produced by the preamplifiers are then inputted to appropriate pulse processing electronics, as generally known in the art. APD-based PET detectors are preferred as they are insensitive to magnetic fields and thus would work well within the magnetic fields produced by the multi-dimensional permanent magnet 205 as shown in FIG. 2.

It should be appreciated by those having ordinary skill in the art that while the present invention has been illustrated and described in what is deemed to be the preferred embodiments, various changes and modifications may be made to the invention without departing from the spirit and scope of the invention. Therefore, it should be understood that the present invention is not limited to the particular embodiments disclosed herein.

What is claimed is:

1. A positron-confined positron emission tomography (PET) imaging apparatus, comprising:
    a multi-axis magnet for generating a multidimensional, static magnetic fields, so as to confine a range of positrons emitted from an object being imaged to within said magnetic fields in each of a plurality of dimensions; and
    a PET detector module including a scintillator and a photodetector optically coupled to said scintillator, said PET detector module being disposed within said magnetic fields.

2. A positron-confined positron emission tomography (PET) imaging apparatus as set forth in claim 1, further including a plurality of said PET detector modules arranged in a ring configuration within said magnetic field.

3. A positron-confined positron emission tomography (PET) imaging apparatus as set forth in claim 1, wherein said photodetector is a solid-state photodetector.

4. A positron-confined positron emission tomography (PET) imaging apparatus as set forth in claim 3, wherein said solid-state photodetector is an avalanche photodiode (APD).

5. A positron-confined positron emission tomography (PET) imaging apparatus as set forth in claim 3, wherein said solid-state photodetector is a silicon-based photodetector.

6. A positron-confined positron emission tomography (PET) imaging apparatus as set forth in claim 3, further comprising a preamplifier for collecting an electric charge generated by said solid-state photodetector in response to scintillation events.

7. A positron-confined positron emission tomography (PET) imaging apparatus as set forth in claim 6, wherein said preamplifier is selected from the group consisting of a charge sensitive preamplifier, a transimpedance preamplifier, and a voltage sensitive preamplifier.

8. A positron-confined positron emission tomography (PET) imaging apparatus as set forth in claim 1, wherein said multi-axis magnet is a three-axis magnet.

9. A positron-confined positron emission tomography (PET) imaging apparatus as set forth in claim 1, wherein said multi-axis magnet is an electromagnet.

10. A positron-confined positron emission tomography (PET) imaging apparatus as set forth in claim 1, wherein the PET detector module is positioned within a bore of the multi-axis magnet.

11. A method of improving spatial resolution of PET images reconstructed from PET data acquired by PET detectors, comprising placing said PET detectors within a bore of a multi-axis magnet generating multi-dimensional, static magnetic fields, so as to confine a range of positrons emitted from an object being imaged by said PET detectors to within said magnetic fields in each of a plurality of dimensions.

12. A method as set forth in claim 11, wherein said magnet is a three-axis magnet producing magnetic fields in three dimensions.

13. A method as set forth in claim 11, wherein said magnet is an electromagnet.

* * * * *